United States Patent
Wisser et al.

(10) Patent No.: US 11,318,031 B2
(45) Date of Patent: May 3, 2022

(54) DEVICE FOR FEEDING AND SETTING AN IMPLANT INTO A BLOOD VESSEL

(71) Applicant: MEDIZINISCHE UNIVERSITÄT WIEN, Vienna (AT)

(72) Inventors: Wilfried Wisser, Vienna (AT); Marie-Elisabeth Stelzmüller, Vienna (AT)

(73) Assignee: MEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 17/415,220

(22) PCT Filed: Dec. 19, 2019

(86) PCT No.: PCT/EP2019/086153
§ 371 (c)(1),
(2) Date: Jun. 17, 2021

(87) PCT Pub. No.: WO2020/127626
PCT Pub. Date: Jun. 25, 2020

(65) Prior Publication Data
US 2022/0079789 A1    Mar. 17, 2022

(30) Foreign Application Priority Data
Dec. 20, 2018 (WO) ................. PCT/EP2018/086246

(51) Int. Cl.
*A61F 2/966* (2013.01)
*A61F 2/95* (2013.01)

(52) U.S. Cl.
CPC ............ *A61F 2/966* (2013.01); *A61F 2/9522* (2020.05); *A61F 2002/9511* (2013.01); *A61F 2002/9665* (2013.01)

(58) Field of Classification Search
CPC ................... A61F 2/966; A61F 2/9522; A61F 2002/9511; A61F 2002/9665
See application file for complete search history.

(56) References Cited

U.S. PATENT DOCUMENTS

| 6,514,280 B1 | 2/2003 | Gilson |
|---|---|---|
| 2009/0264993 A1 | 10/2009 | Greenan |

(Continued)

FOREIGN PATENT DOCUMENTS

| DE | 10 2012 110 861 | 5/2014 |
|---|---|---|
| JP | 2002-510525 | 4/2002 |

(Continued)

OTHER PUBLICATIONS

Japanese Office Action dated Nov. 9, 2021 issued in Japanese Patent Application No. 2021-534197 and English translation, 4 pp.

(Continued)

*Primary Examiner* — Elizabeth Houston
*Assistant Examiner* — Michael G Mendoza
(74) *Attorney, Agent, or Firm* — Nixon & Vanderhye P.C.

(57) ABSTRACT

A device for feeding and setting an implant into a blood vessel includes a hollow cylindrical portion formed of an expandable wire mesh netting with a first end and a second end, with a sleeve for receiving the implant in a radially compressed state. The sleeve is arrangeable along a guide wire. The sleeve for receiving the implant in the radially compressed state is formed by an inner sleeve, around which at least one outer sleeve with a distal end and a proximal end is arranged. The implant is arranged in the inner sleeve in such a way that the second end of the hollow cylindrical portion is arranged on the end facing the proximal end of the outer sleeve, so that during setting of the implant, the inner sleeve surrounding the implant can be moved into the outer (Continued)

sleeve in the distal direction so that the implant expands, beginning from the second end.

7 Claims, 5 Drawing Sheets

(56) References Cited

U.S. PATENT DOCUMENTS

| | | | |
|---|---|---|---|
| 2009/0270965 A1 | 10/2009 | Sinha et al. | |
| 2011/0208292 A1* | 8/2011 | Von Oepen | A61F 2/97 623/1.23 |
| 2011/0301685 A1 | 12/2011 | Kao | |
| 2011/0307049 A1* | 12/2011 | Kao | A61F 2/966 623/1.11 |
| 2014/0379065 A1* | 12/2014 | Johnson | A61F 2/958 623/1.11 |
| 2015/0057738 A1 | 2/2015 | Hepke et al. | |
| 2017/0056215 A1 | 3/2017 | Nagesh et al. | |

FOREIGN PATENT DOCUMENTS

| | | |
|---|---|---|
| JP | 2013-528112 | 7/2013 |
| WO | WO 2014/188412 | 11/2014 |
| WO | 2016/164215 | 10/2016 |
| WO | WO 2016/164215 | 10/2016 |

OTHER PUBLICATIONS

International Search Report dated Mar. 16, 2020 issued in PCT International Patent Application No. PCT/EP2019/086153, 4 pp.
International Search Report and Written Opinion dated Aug. 8, 2019 issued in PCT International Patent Application No. PCT/EP2018/086246, 12 pp.

* cited by examiner

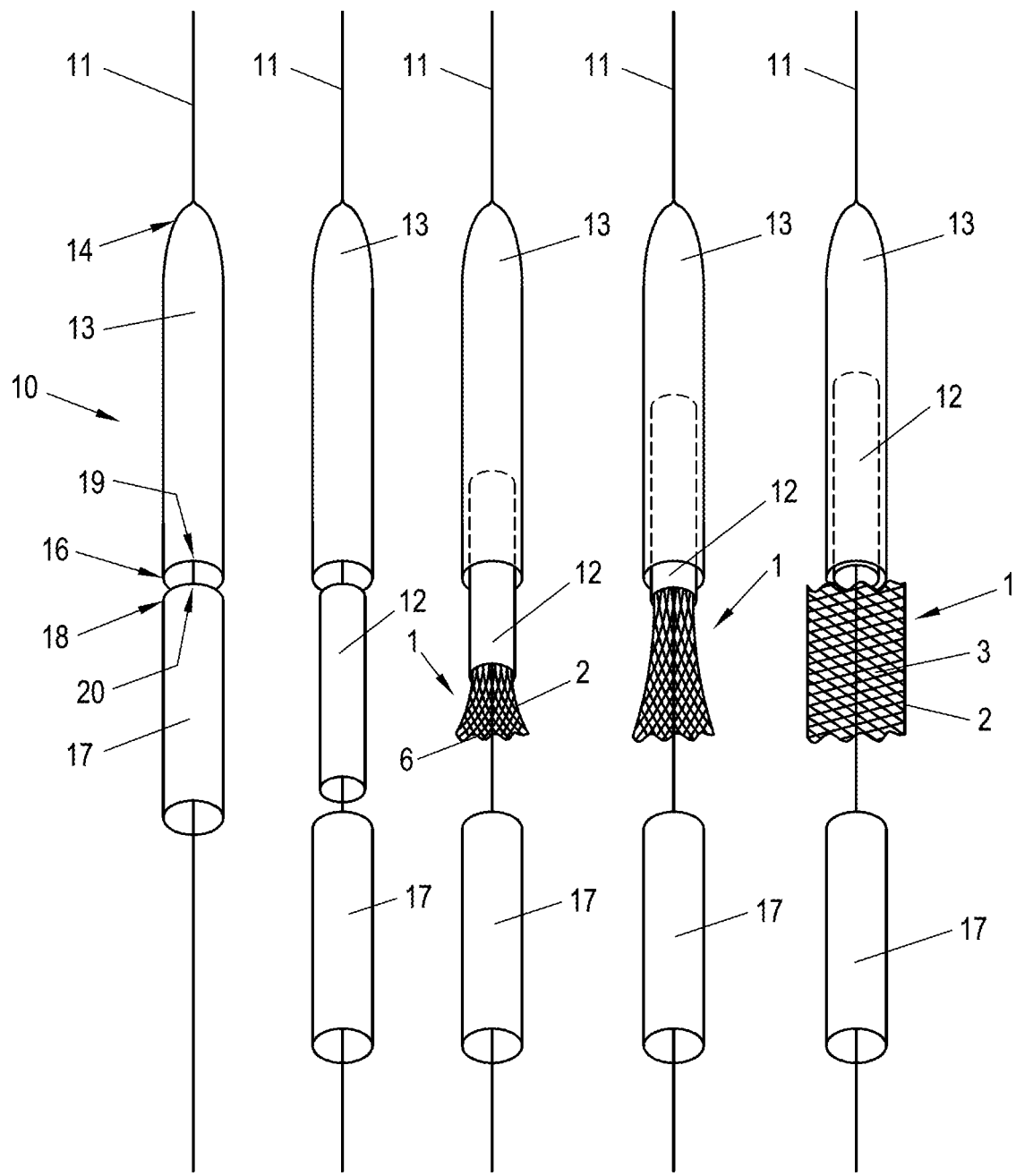

DEVICE FOR FEEDING AND SETTING AN IMPLANT INTO A BLOOD VESSEL

This application is the U.S. national phase of International Application No. PCT/EP2019/086153 filed Dec. 19, 2019 which designated the U.S. and claims priority to PCT International Application No. PCT/EP2018/086246 filed Dec. 20, 2018, the entire contents of each of which are hereby incorporated by reference.

The invention relates to a device for feeding and setting a compressible implant with a hollow cylindrical portion made of an expandable wire mesh netting having a first end and a second end into a blood vessel, the device comprising a sleeve for receiving the implant in a radially compressed state, said sleeve being arrangeable along a guide wire.

The term implant covers, in particular, stents or vascular supports, stent grafts, heart valves or suchlike, which are inserted into a blood vessel in order to keep the latter open or to support or replace functions within the blood vessel or the heart. Common to the implants, is a hollow cylindrical portion made of a self-expanding wire mesh netting, which is inserted into the vessel in the radially compressed state and, in the expanded state, remains at the desired position in the vessel. Stents essentially comprise only the self-expanding wire mesh netting and are inserted into blood vessels in order to keep these open. Stent grafts combine the function of a stent with the function of a vascular prosthesis in that at least one part of the self-expanding wire mesh netting is provided with a fabric sheathing. Heart valves with a hollow cylindrical portion made of a self-expanding wire mesh netting, within which the heart valve is arranged, also come under the term implants used here, even though they are not arranged in the blood vessel itself, but in the heart. With the aid of the self-expanding wire mesh netting, the heart valves are supported at the desired position in the heart and perform the corresponding valve function.

In addition to implants for blood vessels, compressible implants for other vessels or hollow organs, such as the oesophagus, which are insertable with the present device, are theoretically conceivable for supporting diseased tissue.

For example, the interventional treatment of vascular pathologies using stent grafts is an established procedure. The most frequently occurring pathologies include aneurysms, i.e. expansions of the cross-section of the blood vessels, and dissections of blood vessels, i.e. tearing of the vascular inner wall. Acute tearing of the ascending aorta, known as type A dissection of the ascending aorta, is an acute life-threatening condition that requires an immediate operation. The operation requires cooling of the patient (hypothermia) and a phase of circulatory arrest, during which the brain must be selectively supplied with blood (antegrade cerebral perfusion). Depending on the initial situation, the intraoperative mortality rate is between 15% and 30%. Fundamentally, rapid treatment or staving off of the treat to life is desirable. Whereas treatment of the descending aorta by means of stent grafts is frequently carried out, there are hardly any implants available for the ascending aorta, and these can only be used to a limited extent and at high risk, as exact positioning of the vascular prosthesis very close to the aortic valve and the coronary vessel branches is problematical.

For example, DE 10 2012 110 861 A1 describes an endovascular stent prosthesis which is also suitable for arranging in the aortic arch.

WO 2014/188412 A2 relates to a stent graft for the ascending aorta in which special extensions with openings for coupling to coronary vessels are provided. The exact positioning of the stent graft from the vessels in the groin poses an extreme challenge for the surgeon. Furthermore, the construction of the stent graft is extremely complex and it would have to be specially made for the anatomy of the person in question, which does not allow use in an emergency situation.

Finally, US 2009/0264993 A1 shows a vascular prosthesis for the ascending aorta for use in the case of dissection of the aorta with, at the proximal end, a plurality of anchors with hooks arranged thereon. However, the shape of the proximal end increases the risk of damage to the vascular inner wall or even the aortic valve. The disclosed feed device for the stent graft only allows exact positioning in the case of implantation via the aortic arch.

Another form of embodiment of a device of this type, with coaxial sleeves for feeding and setting an implant into a blood vessel, is described in U.S. Pat. No. 6,514,280 B1. When setting the implant into a blood vessel, the inner sleeve is pushed in the proximal direction into the outer sleeve, through which the implant expands, beginning from the furthermost point.

In all the hitherto approved methods of feeding and setting an implant into a blood vessel, more particularly a stent graft into the ascending aorta, exact positioning of the implant at the desired point of the implant, for example positioning the stent graft just above the aortic valve, is problematic, and is not, or is only inadequately supported by present implants. In addition, a stent graft for the ascending aorta is inserted from the blood vessels in the groin which means that the aortic arch has to be overcome.

The object of the present invention is therefore to provide a device for feeding and setting an implant into a blood vessel, through which exact and simple positioning of the implant at the desired point in the blood vessel is made possible. The device for feeding and setting the implant should be constructed as simply as possible in order to allow easy and cost-effective manufacturing as well as a wide range of applications, in particular in cases of emergency. The drawbacks of known devices should be avoided or at least reduced.

The task according to the invention is solved by an aforementioned device for feeding and setting an implant into the blood vessel, wherein the sleeve for receiving the implant in the radially compressed state is formed by an inner sleeve, around which at least one outer sleeve having a distal end and a proximal end is arranged, wherein the implant is arranged in the inner sleeve in such a way that the second end of the hollow cylindrical portion is arranged on the end facing the proximal end of the outer sleeve, such that during the setting of the implant, the inner sleeve surrounding the implant can be moved into the outer sleeve in the distal direction so that the implant expands, beginning from the second end. The device according to the invention allows the insertion of an implant into a blood vessel with simple and rapid exact positioning of the implant in the blood vessel. The more exact positioning of the implant during setting into the blood vessel is possible because the implant is successively opened and expanded, beginning from the proximal end. Expansion of the implant thus takes place in the direction of feeding the device into the respective blood vessel. The device for feeding and setting the implant is relatively simply constructed and can therefore be cost-effectively manufactured. The device can be inserted both in the direction of the blood flow, i.e. in an antegrade manner, and against the direction of the blood flow, i.e. in a retrograde manner. The device supports the treatment of the patient, particularly in an acute case. More particularly, the setting of a stent graft for the ascending aorta from the heart muscle is possible with the device according to the invention, as the left ventricle is perforated and the device is fed into the ascending aorta through the aortic valve. Through this, access from the groin vessels can be avoided, as a result of which overcoming the curvature of the aortic arch and dangerous damaging of the already impaired vessel are eliminated. Furthermore, more exact positioning of the stent graft is possible during setting from the heart muscle, as the stent graft is successively opened and expanded starting from a position just above the aortic valve. Setting of the stent graft is therefore possible irrespective of the condition (size, twisted course etc.) of the groin vessels and the extent of the dissection. The device according to the invention allows the feeding and setting, i.e. opening of the stent graft, and thus securing of the dissection lamella, starting directly above the aortic valve in the direction of the blood flow (from proximal to distal). As result the risky area of the aortic root is secured and the danger of displacing the coronary vessels (coronary ostia) branching from the aortic root is considerably reduced.

The distal end of the outer sleeve of the device for feeding and setting the implant is preferably configured to be rounded or pointed. Through such a design measure, the setting of the implant into the respective blood vessel is facilitated.

If openings are arranged at the distal end of the outer sleeve of the feeding device, an unhindered blood flow can be assured by the device during the surgical intervention. Moreover, through such openings, the weight of the device can be reduced.

Advantageously, a second sleeve provided, or the outer sleeve is designed in two parts. Through such division into two parts, a larger curvature of the entire device is achieved as a result of division of the length and consequently the surgical intervention can be simplified.

If a coupling element is provided at the proximal end of the outer sleeve, and a coupling element shaped complementarily thereto is provide at the distal end of the second sleeve for coupling the outer sleeve with the second outer sleeve, the two portions of the outer sleeve of the device can be connected to each other in an easily detachable manner.

The coupling elements can, for example, be formed by radial steps and/or magnets. In this way, the outer sleeve, comprising two parts, can be inserted at the desired point in the blood vessel in a jointly coupled state and then easily separated during the course of setting the implant.

The present invention will be described in more detail with the aid of the attached drawings. In these:

Figure 7:
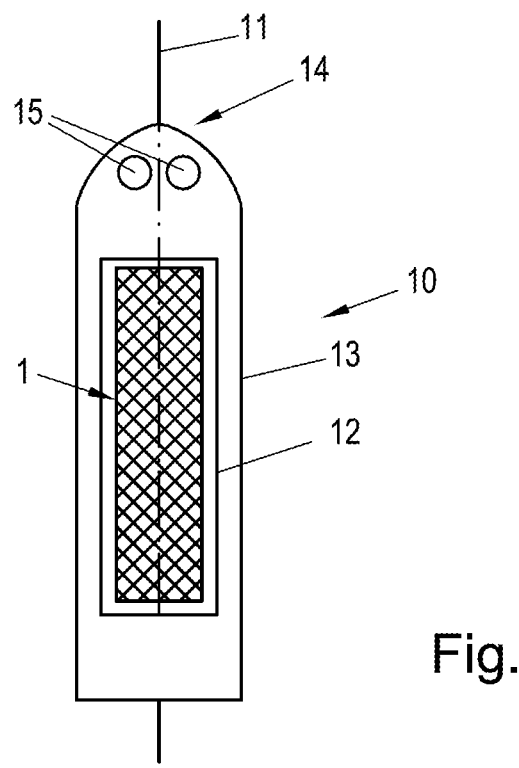
FIG. 7 shows a schematic and partial cross-sectional view of a device according to the invention for setting an implant into a blood vessel.
Figure 13A:
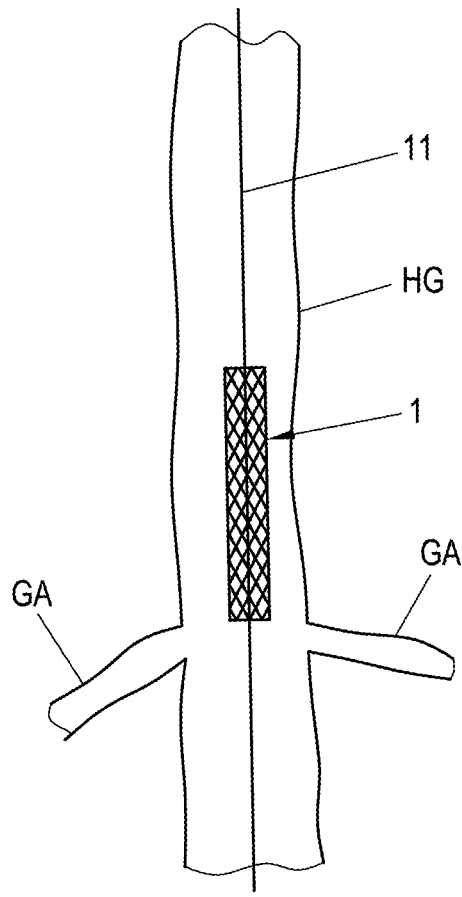
Figure 13B:
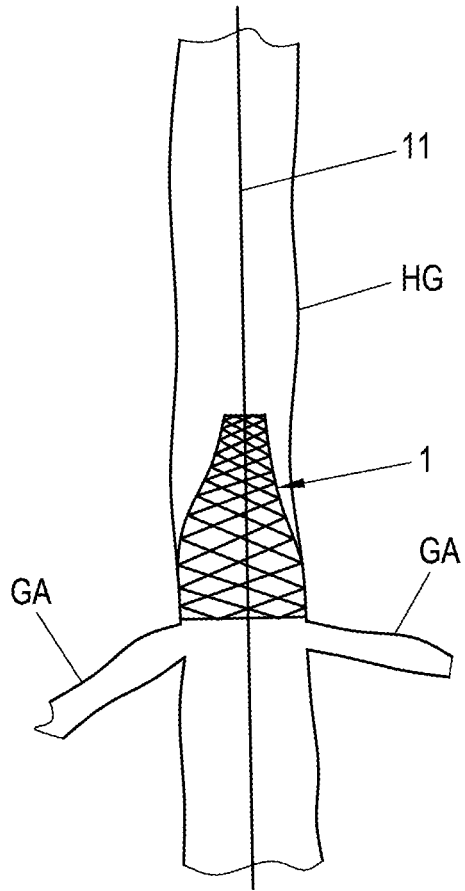
Figure 14:
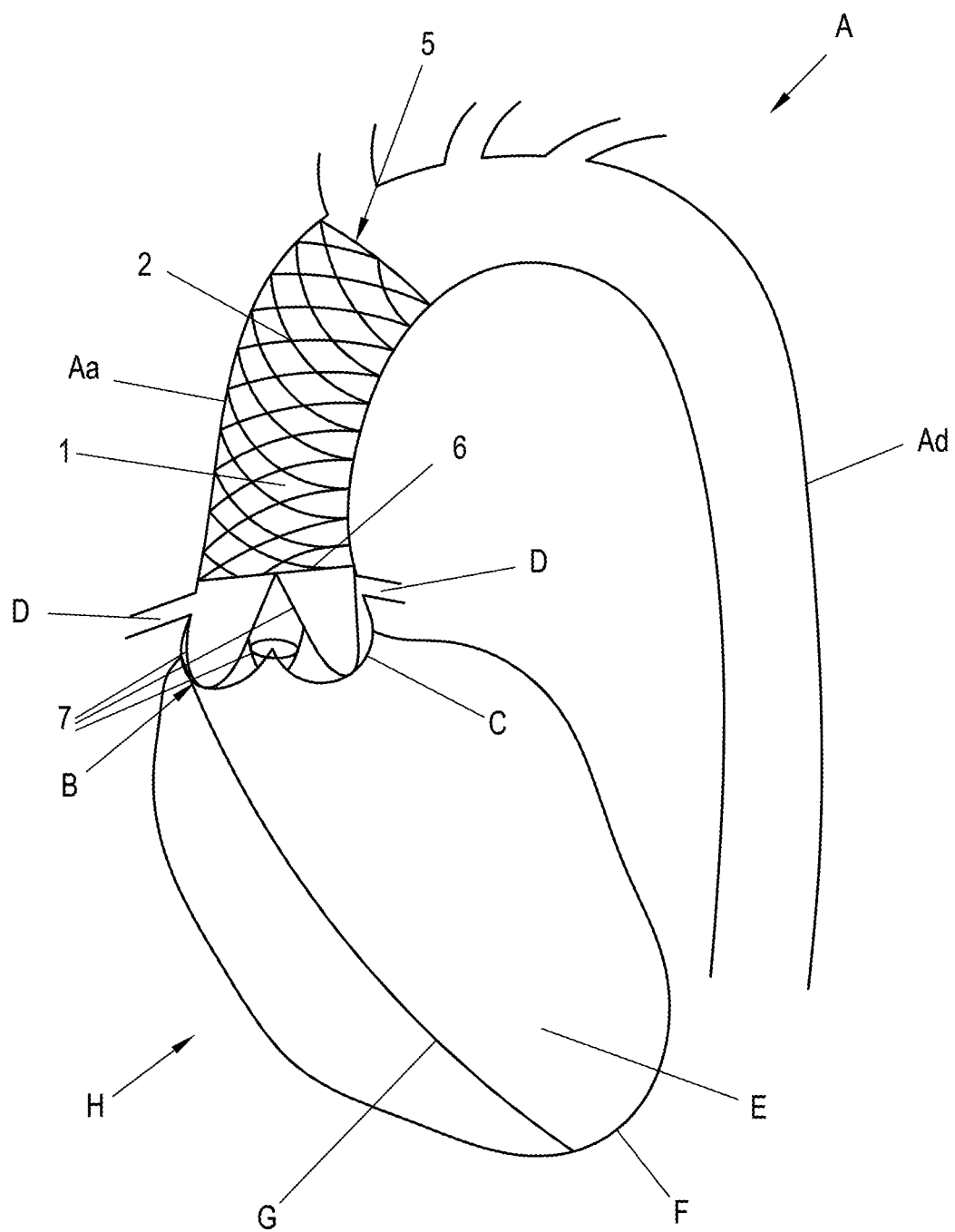

FIG. 8 to FIG. 12 schematically show various states during the setting the implant into a blood vessel with a device according to FIG. 7;

FIG. 13A shows a schematic view of the setting of a stent as an implant into a blood vessel, wherein the stent is radially compressed;

FIG. 13B shows a further schematic view during setting of a stent into a blood vessel, wherein the stent is already partially in the expanded state; and FIG. 14 shows a stent graft arranged as an implant in the ascending aorta.

Figure 1:
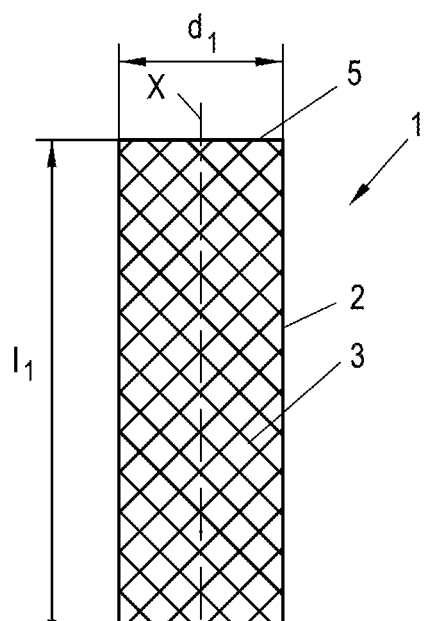
FIG. 1 shows a side view of a stent as a possible implant in the radially compressed state.

Shown in FIG. 1, is a side view of a stent as an implant 1 for a blood vessel in a radially compressed state. The stent as implant 1 includes a hollow cylindrical portion 2 made of a self-expanding wire mesh netting 3, more particularly a shape-memory alloy, preferably nitinol. The hollow cylindrical portion 2 has a first end 5 and a second end 6. In the radially compressed state, the stent has a total length $l_1$ and a diameter $d_1$.

Figure 2:
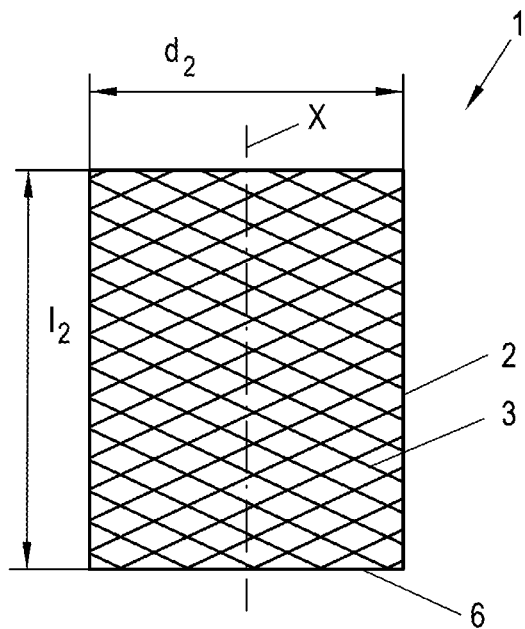
FIG. 2 shows a side view of the stent according to FIG. 1 in the radially expanded state.

FIG. 2 shows a side view of the stent according to FIG. 1 in the radially expanded state. In the expanded state, the stent has a total length $l_2$ and a diameter $d_2$.

Figure 3:
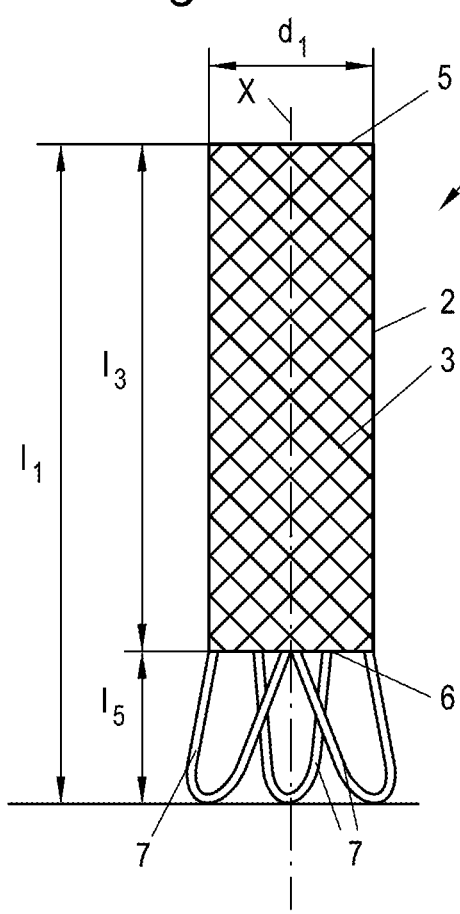
FIG. 3 shows a side view of a stent graft for the ascending aorta as a further implant in the radially compressed state.

Shown in FIG. 3 is a side view of a stent graft as a further possible implant 1 for the ascending aorta Aa in the radially compressed state. Like the stent in accordance with FIGS. 1 and 2, the stent graft comprises a hollow cylindrical portion 2 made of a self-expanding wire mesh netting 3, more particularly a shape-memory alloy, preferably nitinol. The hollow cylindrical portion 2 is surrounded by a fabric sheathing 4, for example of polymer fibre fabric. The hollow cylindrical portion 2 has a first end 5 and a second end 6. Arranged on the second end 6 of the hollow cylindrical portion 2 of the stent graft, which in the implanted state is the end 6 facing the aortic valve C (see FIG. 14), are precisely three spacer elements 7 for adjusting the distance of the second end 6 of the hollow cylindrical portion 2 from the aortic valve C. The three spacer elements 7 correspond to the arrangement of the three leaflets of the aortic valve C, through which exact positioning as close as possible to the aortic valve C or the commissure is guarantee by the predetermined length of the spacer elements 7. The hollow cylindrical portion 2 with the fabric sheathing 4, arranged above the spacer elements 7, is thereby placed as close as possible above the attachment of the aortic valve leaflets (commissure abutments) in the ascending aorta Aa. Such a stent graft is relatively simple to manufacture and can be supplied in different sizes so that in acute cases the implant is immediately available.

In the radially compressed state, the stent graft preferably has a total length $l_1$ of between 50 mm and 100 mm and length $l_3$ of the hollow cylindrical portion 2 of between 40 mm and 90 mm. The diameter $d_1$ in the radially compressed state is usually between 5 mm and 12 mm. Looking in the direction of the longitudinal axis X of the stent graft, the spacer elements 7 have a length $l_5$ which in correspondence with the anatomy of the heart is between 10 mm and 30 mm.

Viewed from above, the spacer elements 7 are preferably arranged at uniform angular distances of essentially 120°. As has already been mentioned above, in the case of anatomical defects of the aortic valves (bicuspid aortic valves), variants with two spacer elements 7 with angular distances of 180° are also possible (not shown).

Figure 4:
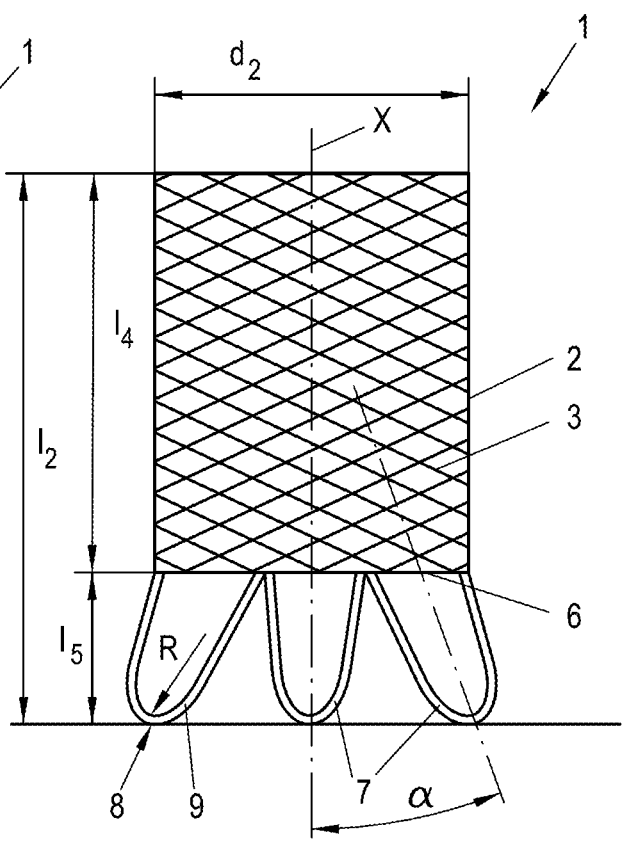
FIG. 4 shows a side view of the stent graft according FIG. 3 in the radially expanded state.

FIG. 4 shows a side view of stent graft according to FIG. 3 in the radially expanded state. In the expanded state the stent graft has a total length $l_2$ of preferably 40-90 mm and a diameter $d_2$ of between 20 mm and 60 mm. The hollow cylindrical portion 2 has a length $l_4$ of between 30 mm and 80 mm. In the radially expanded state, the spacer elements 7 are preferably arranged protruding at an angle α of between 10° and 30°. Through this it is ensured that when the stent graft is set, the function of the leaflets of the aortic valve C is not impaired. The free end 8 of the spacer elements 7 is preferably rounded in design, more particularly with a radius R of between 8 mm and 25 mm. The distance elements 7 are preferably formed of wire loops 9, which, in particular, are made of the same material as the wire mesh netting 3 of the hollow-cylindrical portion 2. This material is, in particular, a shape-memory alloy, preferably nitinol, a nickel-titanium alloy. This involves special metals which from the compressed state automatically transform into an expanded state. In particular, nitinol, a nickel-titanium alloy, constitutes a suitable shape-memory alloy, which is particularly elastic, kink-resistant and flexible.

Figure 5:
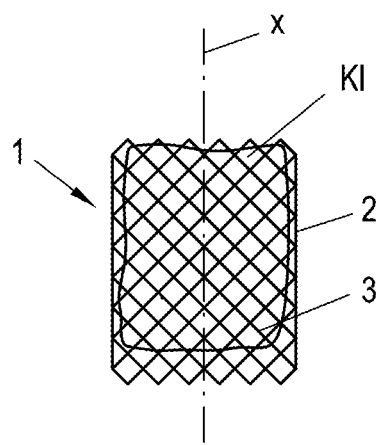
FIG. 5 shows a side view of a biological heart valve as a further implant in the radially compressed state.

In FIG. 5, a side view of a biological heart valve is shown as a further possible implant 1 in the radially compressed state. The heart valve, like a stent or a stent graft, also includes a hollow cylindrical portion 2 made of a self-expanding mesh netting 3, more particularly made of a shape-memory alloy, preferably nitinol. Attached to the wire mesh netting 3 is the valve Kl, in particular a valve made of biological material.

Figure 6:
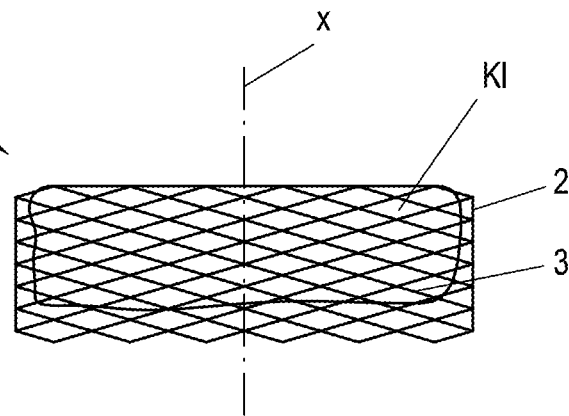
FIG. 6 shows a side view of the heart valve according to FIG. 5 in the radially expanded state.

FIG. 6 shows a side view of the heart valve according to FIG. 5 in the radially expanded state.

FIG. 7 shows a device 10 according to the invention for setting an implant 1 into a vessel or a hollow body, more particularly a blood vessel. These implants 1 include stents, as shown in FIGS. 1 and 2, stent grafts 1 according to FIGS. 3 and 4 or heart valves according to FIGS. 5 and 6. The device 10 comprises an outer sleeve 13 and an inner sleeve 12 for receiving the implant 1 in the radially compressed state. The outer sleeve 13 and the inner sleeve 12 are arranged along a guide wire 11 and placed at the required point in the respective blood vessel. The distal end 14 of the outer sleeve 13 of the device 10 for feeding and setting the implant 1 is preferably configured to be rounded or pointed. Through such a design measure, the setting of the implant 1 through the respective blood vessel is facilitated. If openings 15 are arranged at the distal end 14 of the outer sleeve 13, an unhindered blood flow can be assured by the device 10 during the surgical intervention. In addition, through such openings 15, the weight of the device 10 can be reduced. The number, shape and size of the openings 15 can vary. In accordance with the invention, the device 10 serves to insert the implant 1 into the respective blood vessel and place and release it there as exactly as possible. During setting of the respective implant 1, the sleeve 12 surrounding the implant 1 is moved into the outer sleeve 13 in the distal direction so that the implant 1 expands, starting from the second end 6 of the cylindrical portion 2. This will be explained in more detail below with the aid of FIGS. 8-12.

FIG. 8 to FIG. 12 schematically show various states during the feeding and setting of the implant 1, for example a stent according to FIGS. 1 and 2, into a blood vessel. In this example of embodiment of the device 10, the outer sleeve consists of two parts, namely the outer sleeve 13 and second outer sleeve 17. This form of embodiment reduces the total length of the rigid sleeve compared with a single-part variant of embodiment. As shown in FIG. 8, the second outer sleeve 17 is connected to the proximal end 16 of the first outer sleeve 13. For simpler connection, appropriate coupling elements 19, 20 can be arranged at the proximal end 16 of the outer sleeve 13 or at the distal end 18 of the second outer sleeve 17. These coupling elements 19, 20 can be formed by radial steps and/or magnets (not shown). The distal end 14 of the outer sleeve 13 is preferably rounded or pointed in design. The device 10 shown in FIG. 8 is inserted into the blood vessel with the inner sleeve 12 contained therein which holds the implant 1 in the radially compressed state.

According to FIG. 9, after insertion of the device 10 into the respective blood vessel, the second outer sleeve 17 is removed from the outer sleeve 13, so that the inner sleeve 12, containing the implant 1 in the radially compressed state, is exposed.

Thereafter, according to FIG. 10, the inner sleeve 12 is pushed into the outer sleeve 13, and the implant is successively released, starting from the second end 6 of the hollow cylindrical portion 2. In this way, the implant 1 can be placed exactly at the desired location, for example, above a bifurcation of a branch from the blood vessel.

In the view according to FIG. 11, the implant 1 is almost completely exposed and the inner sleeve 12 of the device 10 is arranged almost completely in the outer sleeve 13.

According to FIG. 12, the implant 1 has been completely exposed so that it has fully expanded due to the self-expanding wire mesh netting 3. As the inner diameter of the hollow cylindrical portion 2 of the implant 1 is now enlarged compared with the radially compressed state, the inner sleeve and the outer sleeve 13 can now be consecutively or simultaneously removed again through the implant 1 and through the blood vessel.

In FIG. 13A, the setting of a stent as an implant 1 into a main blood vessel HG is shown. The main blood vessel HG has two branches GA, above which the stent is to be placed as implant 1. Precise positioning is important as, on the one hand, the branches GA should not be displaced by the stent, but, on the other hand, the distance of the end of the stent from the branches GA should not be too great, so that the damaged main blood vessel HG is also protected there by the stent. With the device 10 according to FIGS. 7 to 12, the stent 1 is inserted into the main blood vessel HG along a guide wire 11.

According to FIG. 13B, at exactly the desired point of the main blood vessel HG, the device 10 is operated so that the stent expands beginning from the proximal end. The sleeve of the device 10 is moved further until the stent has expanded to the distal end. In this way, exact positioning of the stent—here precisely above the branches GA of the main blood vessel HG is made possible. Finally, the device 10 and the guide wire 11 are removed.

Finally, FIG. 14 shows a stent graft according to FIGS. 3 and 4 placed as implant 1 into the ascending aorta Aa. The figure shows the heart muscle H with the septum G and aorta A, divided into the ascending aorta Aa and descending aorta Ad. Through the setting mechanism described in FIGS. 8-12, the stent graft can be optimally placed into the ascending aorta Aa just above the aortic valve C and the branches of the coronary vessels D. The length of the stent graft is selected in such a way that the area of the ascending aorta Aa is covered as much as possible by the implant. Through the spacer elements 7 at the second end 6 of the hollow cylindrical portion 2 of the stent graft, the distance of the second end 6 of the hollow cylindrical portion 2 from the aortic valve C can be precisely adjusted with the fabric sheathing 4. The spacer elements 7 which are not surrounded by the fabric sheathing 4 also allow the branches of the coronary vessels D from the aortic root D to be kept free.

The invention claimed is:

1. A device for feeding and setting into a blood vessel: comprising an implant with a hollow cylindrical portion formed of an expandable wire mesh netting with a first end and a second end, with a sleeve for receiving the implant in a radially compressed state, which sleeve is arrangeable along a guide wire, wherein the sleeve for receiving the implant in the radially compressed state is formed by an inner sleeve, around which at least one outer sleeve with a distal end and a proximal end is arranged, wherein the implant is arranged in the inner sleeve in such a way that the first end of the hollow cylindrical portion is arranged on an end facing the proximal end of the outer sleeve, so that during setting of the implant, the inner sleeve surrounding the implant can be moved into the outer sleeve in the distal direction so that the implant expands, beginning from the second end.

2. The device according to claim 1 wherein the distal end of the outer sleeve is rounded in design.

3. The device according to claim 1, wherein openings are arranged at the distal end of the outer sleeve.

4. The device according to claim 1, wherein a second outer sleeve is provided.

5. The device according to claim 1, wherein a coupling element is provided at the proximal end of the outer sleeve, and a coupling element shaped complementarily thereto is provided at the distal end of the second outer sleeve in order to couple the outer sleeve to the second outer sleeve.

6. The device according to claim 5, wherein the coupling elements are formed by radial steps.

7. The device according to claim 5, wherein the coupling elements are formed by magnets.

* * * * *